Dec. 28, 1965 L. M. WEETMAN ETAL Plant Pat. 2,584
SUGAR CANE PLANT
Filed Sept. 16, 1964 3 Sheets-Sheet 1
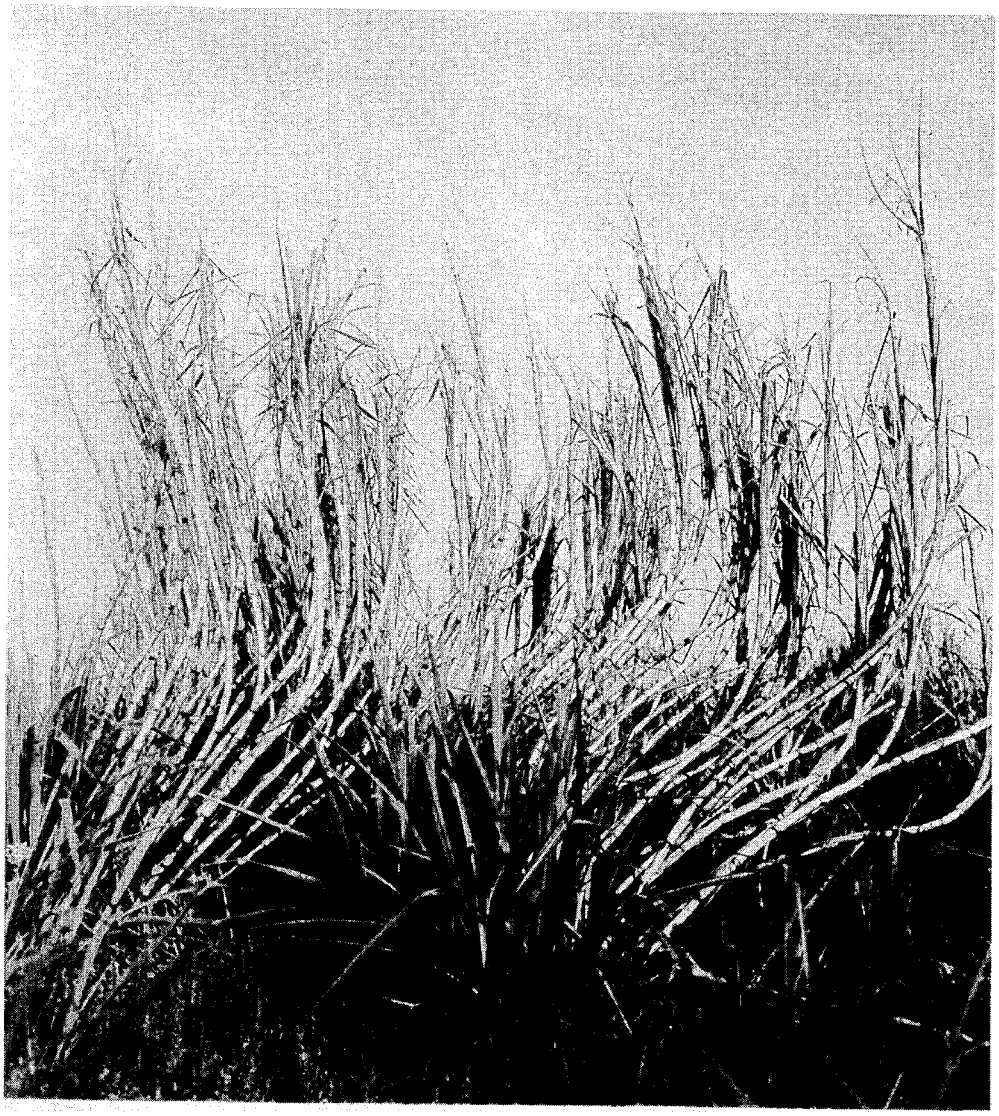
FIG. I
INVENTORS
LESLIE M. WEETMAN
BY BENJAMIN A. BOURNE
Cushman, Darby & Cushman
ATTORNEYS SUGAR CANE PLANT
Filed Sept. 16, 1964
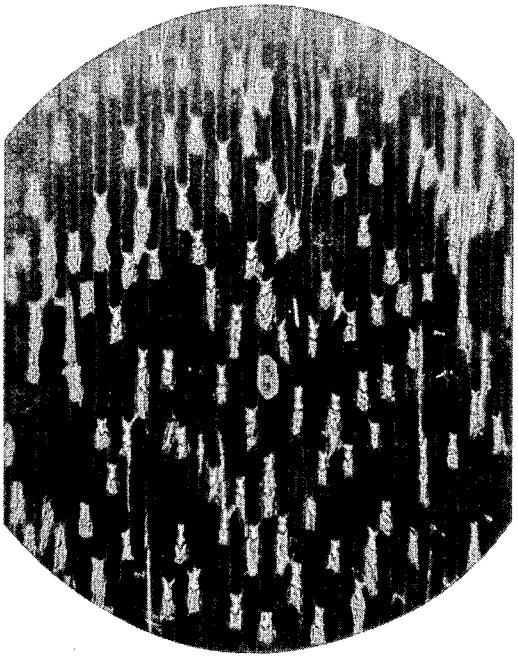
FIG. III
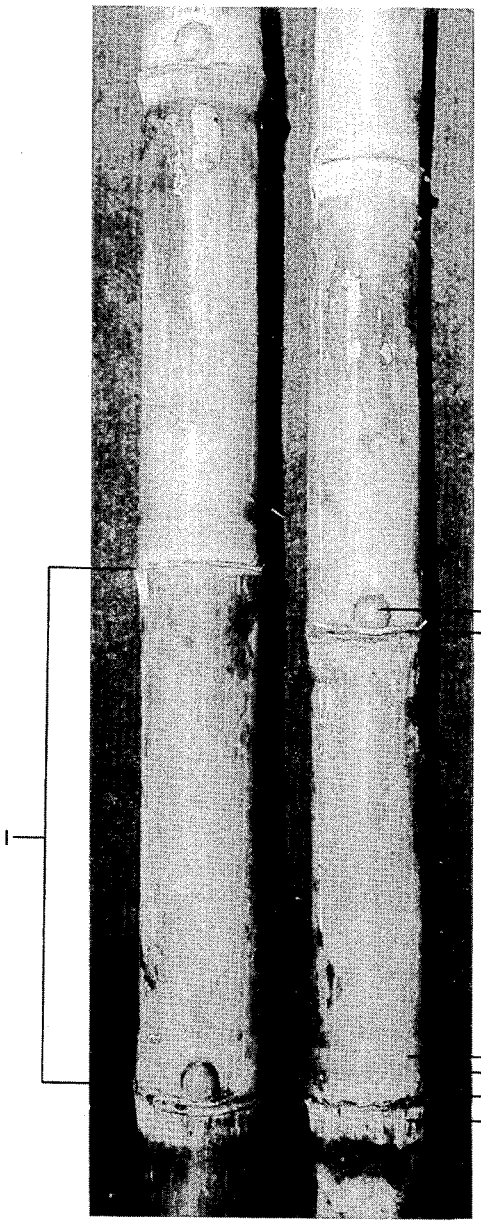
FIG. II
INVENTORS
LESLIE M. WEETMAN
BY BENJAMIN A. BOURNE
Cushman, Darby & Cushman
ATTORNEYS

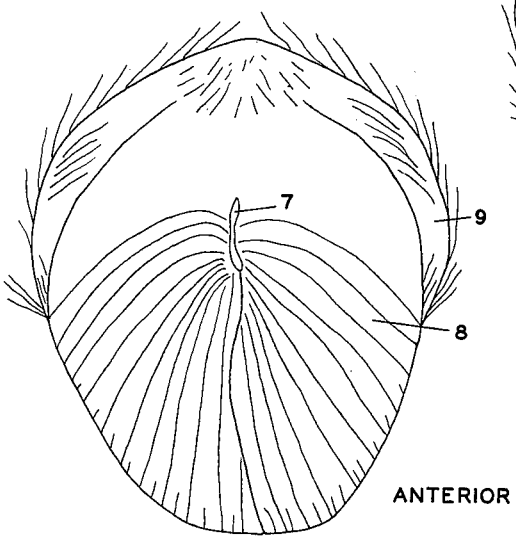
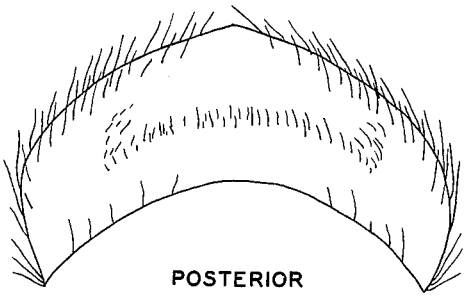
FIG. IV
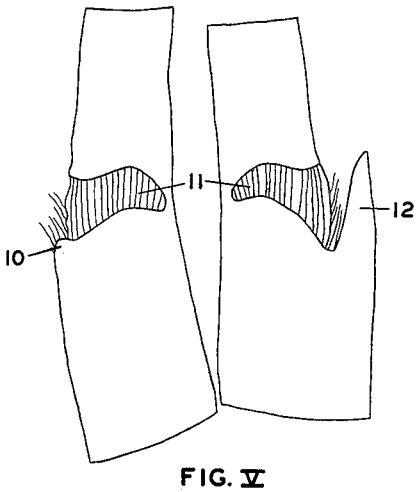
FIG. V
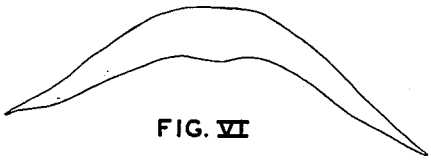
FIG. VI
INVENTORS
LESLIE M. WEETMAN
BY BENJAMIN A. BOURNE
Cushman, Darby & Cushman
ATTORNEYS United States Patent Office Plant Pat. 2,584
Patented Dec. 28, 1965

2,584
SUGAR CANE PLANT

Leslie M. Weetman and Benjamin A. Bourne, Clewiston, Fla., assignors to United States Sugar Corporation, Clewiston, Fla., a corporation of Delaware Filed Sept. 16, 1964, Ser. No. 397,044
1 Claim. (Cl. Plt.—89)

This new variety of sugar cane originated as a seedling produced by the inventors by crossing the variety Cl. 49–54 as female and the variety Cl. 47–83 as male. (In this form of variety designation, which is well known to sugar cane breeders, "Cl." denotes the breeding locality or station, i.e., Clewiston, Florida; "47" represents the year that the particular variety was first grown, i.e., 1947; and "83" is the distinctive number assigned to that variety among those grown in that year.) The cross was made in December 1953 at Clewiston, Florida, and this new variety was selected from among the progeny of this cross. The inventors have subsequently propagated the variety at Clewiston, Florida, by means of stem cuttings under the identifying number Cl. 54–336.

In a replicated variety trial extending over three crop years, juice analyses were made in early November and again in February each year. Average indicated yields of 96° sugar per ton of cane were 214 pounds for the November analyses and 236 pounds for the February analyses. These data indicate medium early maturity and attainment of high sucrose content for medium and late harvest. This variety is also vigorous and produces a high tonnage of cane per acre. It is particularly outstanding in its relative yield on cold marginal land.

Our new variety was planted on cold marginal land consisting of typical low-mineral organic Everglades peat in August 1962. In mid December and toward mid January, it was subjected to below freezing temperatures on several successive days whereby all above-ground parts of the cane were killed. Subsequently the variety grew up again to a perfect stand and with unusually good vigor and stooling, indicating that it is highly resistant to winter killing.

This variety has been exposed repeatedly to natural infection by all the four strains of mosaic disease known in Florida, viz: A, B, D and E (atypical) for more than 2 years and none of the plants has become infected. However, in one test, when using a high pressure spray technique for artificial inoculation with a mixture of all the above strains of the virus, involving 35 plants, it was possible to infect 17.1 percent after an incubation period of 73 days, whereas the variety used for control showed 50% of the 18 inoculated plants to be diseased after this same period. It has been concluded, therefore, that the new variety is highly resistant to natural infection by existing vectors of the four strains of mosaic disease present in Florida and only moderately susceptible to a mixture of these virus strains when inocluated artificially my means of a high pressure spray.

Since the ratoon stunting disease (generally abbreviated RSD) virus is known to be very important in reducing the yield of sugar cane when very susceptible varieties are infected, a series of randomized block field tests was studied with this variety, replicated five times in order to determine the effect of hot air heat treatment at 50° C. for 24 hours on propagating stalk material for the purpose of destroying the ratoon stunting virus. The non-heated propagation stalk material used for comparison was inoculated with the RSD virus by soaking the cuttings in freshly expressed stalk juice of a heavily diseased variety. The field tests were run for both plant cane (1st crop) and as first stubble crop cycles. A statistical analysis was made of the yield data and it showed that while the average tonnage of cane from RSD-free plots was slightly higher than that from the RSD plots, both as plant cane and 1st stubble, the differences were not significant. In regard to the quality of sugar cane as measured by pounds of 96° sugar yielded per ton of cane, if harvested as plant cane in mid-November or on January 7 as 1st stubble, this factor was not significantly affected, although the RSD plots averaged silghtly higher than the RSD-free ones in both instances. However, it was discovered that if the first stubble cane became frozen in mid December, subsequent RSD infected cane suffered a 27.8% reduction in this quality factor after a lapse of 44 days between January 7 and February 20, whereas the plots heat treated for destruction of the RSD virus suffered a yield reduction of 96° sugar in cane of only 6.8%. Statistically the difference was found to be highly significant. Because of this distinct advantage in rate of deterioration after freezing, unless disease-free stock can be procured, then heat treatment of stalk planting material for RSD control is recommended for use in cold marginal lands where deterioration in sugar content quality after freezing presents a serious problem. For harvesting early in the processing season during late November and early December, heat treatment for RSD control is recommended also, because it had no significant detrimental effect on cane quality and yet provided significant protection from rapid sucrose detrioration in case of freeze damage. In a single replicated trial involving first stubble, cane frozen in mid December and harvested March 1, the yield of 96° sugar per acre of RSD-free cane was significantly higher than RSD cane by 0.62 ton, worth with sugar selling at 6.25¢/lb., $77.50. For calculations of significant differences, the 5% point was used in all the studies made.

In the drawings:

FIGURE I is a photographic view showing the habit of growth of mature cane;

FIGURE II is a photographic view of approximate midsections of typical stalks, showing internode 1, stem bud 2, leaf scar 3, growth ring 4, root band 5, and wax ring 6;

FIGURE III is a photomicrographic view showing the pattern of the stem epidermal cells;

FIGURE IV shows anterior and posterior views of the prophyll (or outermost bud scale) of the stem bud, showing germ pore 7, central disk 8, and wing 9;

FIGURE V is a view of the two separated and flattened halves of the upper part of a leaf sheath, showing the outer auricle 10, the dewlap or blade joint 11, and the inner auricle 12; and FIGURE VI is a view showing the outline of a ligule after its removal from the inner surface of the leaf sheath.

DETAILED DESCRIPTION

In the following detailed description of the new variety of sugar cane, the terminology employed in morphological description and numbering of hair groups is that employed by Artschwager (see Sugarcane (*Saccharum officinarum* L.): Origin, Classification, Characteristics, and Description of Representative Clones by Ernest Artschwager and E. W. Brandes. Agriculture Handbook No. 122. United States Department of Agriculture, 1958). Color descriptions are made by referring to the plates of Maerz and Paul (see A Dictionary of Color, second edition, by A. Maerz and M. Rea Paul. McGraw-Hill Book Company, 1950).

*The stalk (or culm)*

*Habit of growth (see FIGURE I).*—The stalks are at first erect, but they normally lean slightly and recurve in mature cane. The internodes are straightly aligned.

*Size.*—The stalks are usually 8 or 9 or more feet in length in mature plant cane. They are nearly circular in cross-section, averaging 27.4 x 28.5 millimeters in the middle part of the stalk. The larger diameter may vary from 24 to 33 millimeters.

*Flesh.*—The color of the flesh is approximately Maerz and Paul's designation 11–G–2. The flesh frequently contains a slight pithiness. Fiber content averages 11.4% of the weight of the cane.

*Internodes (1, FIGURE II).*—They are nearly cylindrical in shape and vary from about 12 to 19 centimeters in length in the middle parts of the stalks, averaging 13.6 centimeters. There are usually no bud furrows, but sometimes there is a slightly flattened area above the bud. Corky cracks and growth cracks are not evident.

*Color.*—The basic rind color just above the growth ring on unexposed internodes is just a little deeper than Maerz and Paul's 19–G–1. The color becomes more greenish higher on the internode and also becomes overcast with whitish wax. There are also splotches of black mold growth. Freshly stripped stalks give an overal appearance of yellowish-green, splotched with black. Exposed stalks gradually turn reddish in the sunlight. The wax ring (6, FIGURE II) is moderately heavy, with a distinct base.

*Growth ring (4, FIGURE II).*—It is 2 to 4 millimeters in height and slightly tumescent. The color is at first much like the basic color of the internode, but becomes olive-green with age.

*Root band (5, FIGURE II).*—It is straight on the bud side and obconoidal opposite the bud. It averages about 8 millimeters tall on the bud side and 7 millimeters opposite the bud. The color is slightly lighter than the basic internode color. There are 2 (or indistinctly 3) rows of root primordia. The primordia are relatively large and prominent.

*Leaf scar (3, FIGURE II).*—The leaf scar protrudes and is slightly oblique, being tilted under the bud.

*Epidermal cells (FIGURE III).*—The pattern of the stem epidermal cells is basically Artschwager's type 1 in which the small cell groups consist of one cork cell and one silica cell in single pairs. These cells have primarily rectangular ends. However, about 10% of the groups consist of two cork cells and one silica cell, as in type 7. Also, there are about 10% of cork cells with pointed ends, as in type 4. This combination would be designated as pattern 1+7+4 in Artschwager's system. There are about 605 short cell groups per square millimeter, and the long cells average 11.6 microns in width. Only a few stomata are present, averaging about 1.8 per square millimeter.

*Stem buds*

*General characteristics.*—The buds (2, FIGURE II) are usually inserted at the leaf scar, though they sometimes vary and may be attached slightly below or above the leaf scar. The tips of the buds usually extend to the growth rings. The buds are not protruding nor overly prominent and have an average size of about 8 millimeters wide by 9 millimeters tall. The prophyll (FIGURE IV) is roundish ovate with round-pointed tip, or it may be somewhat pentagonal. It has a central germ pore and radial venation.

*Wings of the prophyll (9, FIGURE IV).*—The wing is inserted near or slightly above the middle of the prophyll. The apex is broad and often toothed.

*Pubescence.*—Pubescence is moderately conspicuous on the wings with groups 4, 13, 14, 16, and 26 being more or less prominent. Groups 2, 12, 15, 18, 19, 21, 22, and 23 are also evident in most buds.

*The leaf*

*The blade.*—The blades are ascending in habit. They are dark green in color. The larger leaves on each stalk are 5.4 to 6.5 centimeters wide, averaging 6.0, and are 135 to 153 centimeters long, averaging 145. The ratio of the length of the blade to the width thereof averages 24.2.

*The sheath.*—The sheaths have an average length of 37 centimeters. The older sheaths are mostly self-shedding or easily stripped off. The dorsal field of pubescence (group 57) is small, usually only about 10 millimeters wide by 50 to 70 millimeters long, or it may be absent. The hairs are rather sparse and are mostly deciduous on older sheaths. No other hair groups are evident on the sheath.

*Dewlaps (11, FIGURE V).*—The color of the dewlaps varies from about 15–H–1 to 15–L–2 in the plates of Maerz and Paul. The shape is approximately ascending flaring double-crescent in Artschwager's terminology. The outer surface is heavily coated with wax. About half of the outer surface is covered with group 58 hairs. Group 52 hairs cover the inner surface and may be sparse or rather dense. This group usually extends across the midrib rather sparsely. Group 55 is also present, sometimes as only a few hairs, sometimes prominently. Long hairs of group 51 are often prominent near the margin and may cover a considerable area.

*Auricles.*—The outer auricles (10, FIGURE V) are transitional and vary from sloping to somewhat ascending. The inner auricles (12, FIGURE V) are quite variable, even on the same stalk. On the earliest sheaths near the bases of the stalks they tend to be small or merely transitional. At 4 to 6 feet they are usually long lanceolate to as much as 60 millimeters long, though most are from 20 to 40 millimeters. Above this height they become smaller and may be reduced to 5 millimeters or less on upper sheaths of older cane. There are tufts of hairs on the outer auricle and on the base of the inner auricle.

*Ligules (FIGURE VI).*—The ligule is broad-crescent shaped and is about 5 millimeters tall. The marginal cilia (group 61) are ⅓ to ½ millimeter in length and are uneven in length giving a jagged appearance under magnification. The dorsal surface of the ligule is covered with long appressed hairs which are rather dense and prominent.

*Inflorescence.*—This new variety has flowered very sparingly in Florida and apparently without functional pollen.

Important characteristics which, in combination, help to distinguish this new variety of sugar cane from all other known varieties are:

(1) Medium early maturity.
(2) High sucrose content for mid-season and late harvest in Florida.
(3) Ability to grow back vigorously after freezing of above-ground parts.
(4) High resistance to or tolerance of the ratoon stunting disease virus under normal growing conditions.
(5) Eliminating the ratoon stunting disease virus by means of hot air treatment very significantly retarded the deterioration of sucrose in the mature stalks in the field during the period of 23 to 67 days after being frozen in cold marginal lands.
(6) Moderate susceptibility to a mixture of strains "A," "B," "D," and "E" of sugar cane mosaic virus when inoculated artificially, but high resistance to these strains from natural infection by existing vectors.
(7) Stalks which generally become slightly leaning and recurved at maturity.
(8) Stalks nearly circular in cross-section, with diameters in the middle parts of the stalks averaging about 27.4 x 28.5 millimeters.
(9) Fiber content of the stalks averaging about 11.4%.
(10) Bud furrows usually absent, but sometimes taking the form of slightly flattened areas above the buds.
(11) Growth ring usually 2 to 4 millimeters tall.
(12) There are 2, or indistinctly 3, rows of root primordia.
(13) The stem epidermal pattern is 1+7+4 in Artschwagers terminology.

(14) Stomata rather few in the stem epidermis, averaging about 1.8 per square millimeter.

(15) The prophyll of the stem bud is roundish ovate or somewhat pentagonal in shape, with central germ pore and radial venation.

(16) The wing is inserted at or slightly above the middle of the prophyll.

(17) Blades of the leaves are ascending in habit.

(18) The older leaf sheaths are either self-shedding or easily pulled off.

(19) The dorsal field of pubescence (group 57) on the leave sheaths is small and the hairs are mostly deciduous. No other hair groups are present on the sheath.

(20) The dewlaps are approximately ascending flaring double-crescent in shape.

(21) Hairs cover the inner surface of the dewlap and extend across the midrib.

(22) The outer auricle is transitional and may vary from sloping to somewhat ascending.

(23) The inner auricle is usually lanceolate in shape but is very variable in length.

(24) The ligule is broad-crescent shaped and about 5 millimeters tall.

(25) The marginal cilia of the ligule vary from about ⅓ to ½ millimeter in length and give an uneven appearance.

(26) Flowers are infrequent and male-sterile in Florida.

What is claimed is:

The new and distinct variety of sugar cane herein shown and described, identified by the combination of the characteristics enumerated above.

No references cited.

ABRAHAM G. STONE, *Primary Examiner.*